United States Patent [19]

Cise

[11] 4,029,655

[45] June 14, 1977

[54] METHOD OF PREPARING STABLE STERILE CRYSTALLINE CEPHALOSPORINS FOR PARENTERAL ADMINISTRATION

[75] Inventor: Michael D. Cise, Indianapolis, Ind.

[73] Assignee: Eli Lilly and Company, Indianapolis, Ind.

[22] Filed: Apr. 11, 1975

[21] Appl. No.: 567,224

[52] U.S. Cl. .............................. 260/243 C; 53/25; 424/246
[51] Int. Cl.² ...................................... C07D 501/12
[58] Field of Search ................................ 260/243 C

[56] References Cited

OTHER PUBLICATIONS

The Merck Index, p. 222, (Eighth Edition 1968).

*Primary Examiner*—Nicholas S. Rizzo
*Assistant Examiner*—James H. Turnipseed
*Attorney, Agent, or Firm*—Ralph W. Ernsberger; Everet F. Smith

[57] ABSTRACT

Sterile, essentially crystalline cephalosporins for parenteral administration are prepared by a freeze-drying process wherein, after rapidly cooling a solution of such cephalosporins to at least −15° C. in no more than 3 hours, the frozen solution is held between about <0° C. and about −10° C. until the nucleation of the cephalosporin is substantially complete before subjecting said frozen solution to a high vacuum and a moderate amount of heat to sublime the water therefrom.

11 Claims, No Drawings

METHOD OF PREPARING STABLE STERILE CRYSTALLINE CEPHALOSPORINS FOR PARENTERAL ADMINISTRATION

BACKGROUND OF THE INVENTION

1. Field of Invention

This invention is directed to an improved freeze-drying (lyophilization) process. More specifically the instant invention concerns a freeze-drying process wherein cephalosporins are prepared which are sterile, essentially crystalline and have good storage stability.

2. Prior Art

Freeze-drying is an old and often used process for removing a solvent from a solute. While the process is cumbersome, expensive and slow, it provides a method for removing a solvent without damaging heat labile solutes. Antibiotics and other pharmaceuticals have been processed by freeze-drying procedures for three or more decades and foods, particularly instant coffee, have been prepared by this method for many years. Ordinarily, a solution from which it is desired to recover the solute in a relatively solvent-free state is frozen solid and then subjected to an environment of a high vacuum and the temperature of the environment is raised to provide the units of heat absorbed in the sublimation of the solvent from the frozen solution. The temperature of the environment is kept below that which would result in the meltdown of the frozen solution. In practice, the temperature of the environment is coordinated with the vacuum to produce the highest reasonable sublimation rate, avoiding a melting of the frozen mass.

Water is the solvent generally utilized in a freeze-drying process. Other solvents can be employed but are limited to those which become solid in the range of temperatures which can be practically employed in the process and which will sublime under vacuum.

Although all of the material does not have to be in solution to effectively operate a freeze-drying process, instant coffee being one probable example, this invention is concerned with a process wherein crystalline material is prepared in a freeze-drying procedure from a true solution. In freeze-drying antibiotics and other pharmaceuticals it has been the practice to follow the classic process outlined above; to wit, prepare solution, freeze to solid, subject to high vacuum, add heat, sublime solvent. However, when such a conventional procedure is followed, most cephalosporins come out as amorphous material. A state that is undesirable because, generally, the amorphous powder is not storage stable, even under refrigerated conditions. The basically white amorphous cephalosporin powders quickly begin to deteriorate to a disagreeable yellow. The yellow slowly appears and becomes noticeable in between 4 and 6 weeks at 4° C., and after 6 months at this temperature generally is universal throughout the powder.

The cephalosporins involved in this invention can be recovered from organic solvents, such as ethanol in an essentially crystalline state. These crystals are equally as stable as the crystals prepared by the freeze-drying process of the instant invention However, recovering crystals of the cephalosporins for use in sterile ampoule preparations for parenteral administration poses other problems and conditions which are both inefficient, difficult and costly. For example, there is no effective way known to sterilize the crystals of cephalosporins recovered from organic solvents so the entire crystallization process must be carried out in an aseptic environment. In the large and extensive process required to sterilely crystallize the cephalosporins there are many opportunities for the admittance of foreign materials into the crystals which later on will show up as suspended material in a reconstituted ampoule of the antibiotic. No one has yet developed an apparatus for filling dry material into an ampoule which will measure the material going into each ampoule with as good a consistency and precision as can be routinely achieved with liquid filling equipment.

Accordingly, it is an object of this invention to provide a process of freeze drying cephalosporing, selected from the group consisting of cephalothin sodium, cephaloridine betaine, and cefazolin sodium that will result in sterile essentially crystalline cephalosporins for parenteral administration.

Another object of this invention is to provide a process which will include the sterile liquid filling of a measured volume of a sterile solution of a known concentration of a cephalosporin into an ampoule wherein such cehalosporin is recovered from such solution as an essentially crystalline material for parenteral administration which is storage stable.

Still another object of this invention is to provide an ampoule containing an essentially crystalline cephalosporin which is storage stable and which upon reconstitution for parenteral administration is substantially free of foreign suspended material.

SUMMARY

Now it has been discovered that a storage stable, sterile, essentially crystalline cephalosporin selected from the group consisting of cephalothin sodium, cephaloridine betaine and cefazolin sodium for reconstitution for parenteral administration can be prepared by a freeze-drying procedure comprising the following steps: (a) The cephalosporin is dissolved in water in a concentration of between about 15 and about 40 percent. (b) The cephalosporin preparation from (a) is sterile filtered into a previously sterilized container. (c) The cephalosporin preparation from (b) is rapidly lowered to a temperature below at least −15° C. within an interval not longer than 3 hours. (d) The temperature of the cephalosporin preparation from (c) is raised to between <0° C. and about −10° C. (e) The cephalosporin preparation from (d) is held between <0° C. and about −10° C. until the nucleation of the crystals of said cephalosporin is substantially complete. (f) The cephalosporin preparation from (e) is subjected to an environment in which the pressure is maintained at a maximum of 1mm absolute. And, (g) the temperature of the environment in which the cephalosporin preparation is maintained at a maximum of 1mm absolute is raised to 50° C. or below, subliming the water from the cephalosporin preparation resulting in the recovery of an essentially crystalline cephalosporin having a moisture content of not more than 6.0 percent.

DESCRIPTION OF THE PREPARED EMBODIMENTS

The useful process of the present invention comprises a procedure utilizing a freeze-drying operation wherein an aqueous preparation of a cephalosporin selected from the group consisting of cephalothin sodium, cephaloridine betaine and cefazolin sodium is subjected to a temperature which will rapidly, within a period of no longer than 3 hours, lower the temperature of such preparation to at least −15° C., preferably about −20° C. At this temperature dendritic crystals of ice begin to form in which there is little or no cephalosporin entrained. Then the temperature of the environment in which the cephlosporin preparation is held is raised to between <0° C. and −10° C. The rise in the temperature establishes an environment which is favorable for an increase in the size of the dendritic ice crystals, and the nucleation of the cephalosporin crystals begins.

After the temperature has been raised to between <0° C. and −10° C. the cephalosporin preparation is held at such a temperature for from about 2 to about 48 hours to provide a time interval during which substantially all of the cephalosporin solute is nucleated and essentially all of the liquid water becomes ice in which little or no cephalosporin remains entrained therein. The time required for the nucleation of the various cephalosporins varies. For example, between 12 and 24 hours of exposure to a temperature between <0° C. and −10° C. is required to nucleate substantially all of the cephalothin sodium contained in a cephaloporin preparation undergoing freeze drying. From about 12 to about 48 hours are required to nucleate all of the cephalosporin betaine from a cephalosporin preparation, while a cefazolin sodium nucleation will be substantially complete in between about 2 and about 8 hours; both between <0° C. and about −10° C.

Following the critical steps just described, a conventional freeze-drying operation is employed to sublime the ice leaving sterile cephalosporin crystals having a moisture content of no more than 6 percent. Such crystals have a suitable storage stability; three years or more at room temperature, and are appropriate for reconstitution for parental administration.

The crux of the instant invention is the establishment of conditions which are favorable to and result in the development of dendritic ice crystals rather than crystals having a fine platelet or hexagonal structure. The latter two structures are generally developed by slow cooling. Such structures entrain the cephalosporin therein and in a freeze-drying procedure the cephalosporins are deposited in an amorphous state as the ice is sublimed.

In one aspect of the present invention a sterile, essentially crystalline cephalosporin selected from the group consisting of cephalothin sodium, cephaloridine betaine and cefazolin sodium for reconstitution for parenteral administration is prepared by a method comprising the following steps: (a) The cephalosporin is dissolved in water. (b) The aqueous cephalosporin preparation from (a) is filtered through a sterilizing filter into a previously sterilized container. (c) The preparation from (b) is cooled rapidly to a temperature below at least −15° C. within a period of not more than 3 hours. (d) The preparation from (c) is warmed to a temperature between <0° C. and about −10° C. (e) The preparation from (d) is held at a temperature between <0° C. and −10° C. until the nucleation of the crystals of said cephalosporin is substantially complete. (f) The preparation from (e) is subjected to an environment wherein the pressure is maintained at a maximum of no more than 1mm absolute. (g) The temperature of the environment to which the preparation from (f) is exposed is raised to a maximum of about 50° C., avoiding the melting of such preparation. And, (h) the ice is sublimed from the preparation from (g) until the resulting crystals of said cephalosporin have a moisture content of no more than 6 percent.

Any cephalosporin material, of those included in this invention, which is of a pharmaceutical grade can be dissolved in water to provide the aqueous solution used in the useful process detailed herein. A concentration of the cephalosporin between about 15 and about 40 percent (W/V) is appropriate. Preferably, concentrations of cephalothin sodium between about 15 and about 33 percent (W/V); of cephaloridine betaine between about 20 and about 33 percent (W/V); and of cefazolin sodium between about 20 and about 40 percent (W/V) are satisfactory for use in developing the dendritic crystals of ice which are formed when the conditions which are detailed herein, as those required in practicing this invention, are followed.

The sterilization of the aqueous solutions of cephalosporins can be achieved by filtering such solutions through sterile filtering means known to those skilled in the art and collecting the filtrate in a previously sterilized container. Illustratively, sterile filtering can be effected using a heat sterilized plate and frame filter press equipped with an asbestos pad, or a filtering membrane of cellulose acetate or or nitrate, or a candle having a porosity below 0.22 μm.

The dendritic ice crystals, the formation of which is an essential element of this invention, are achieved by rapidly cooling the sterile cephalosporin preparation to a temperature at least below −15° C. It was found that when this temperature was effected within a 3 hour period from the time the cooling was commenced, the formation of dendritic rather than platelet or hexagon crystals was assured. It was also found that cooling the cephalosporin preparation to a temperature below −20° C. was of no additional benefit, but it is essential that the −15° C. be reached throughout the cephalosporin preparation. To accomplish this need it is required that the temperature of the environment in which the cephalosporin preparation is cooled to at least −15° C. be considerably lower than the −15° C. to achieve this temperature within the 3 hour period. Moreover, the actual size of the individual volume of the preparation to be reduced to the −15° C. level will influence the actual operating temperature to which the preparation is exposed. For example, if the volume of the preparation is a relatively large mass in the frozen state, a substantially lower environment temperature will be required in order to lower the temperature throughout the frozen mass to −15° C. than will be required if the individual volumes are relatively small, such as the volume of a 20 percent solution required in a ampoule to result in a 1g quantity of crystalline cephalosporin being deposited therein at the conclusion of the subliming operation, described hereinafter.

In actual practice it is sometimes the custom to provide a thermocouple in a location approximating the center of the frozen mass to indicate the temperature at that point in such mass. If the temperature at such point is not dropping sufficiently fast to reach the −15° C. temperature within 3 hours, additional refrigeration can be added to accomplish the required temperature in the specified time.

Once the −15° C. temperature has been achieved, the physical conditions conducive to the development and propagation of dentritic ice crystals have been established. At this temperature the nucleation of the various cephalosporin crystals will proceed at different rates. In any event, though, nucleation is slower at lower temperatures. To advance the rate of nucleation the temperature is raised to a level that is conducive to the growth of the dendritic crystals and a reasonable rate of nucleation of the cephalosporin crystals. However, the temperature must not be raised to a point where the frozen mass will begin to melt. Therefore, a temperature range of between <0° C. and about −10° C. was found to be effective for completing the crystal nucleation. A temperature of about −8° C. was found to be especially suitable for the cephalosporins involved in this invention. The symbol < used throughout this specification means below; for example, <0° C. means below zero Celsius; i.e., cold enough to maintain the cephalosporin preparation in the frozen state.

The frozen mass of cephalosporin preparation is held at between <0° C. and −10° C., preferably about −8° C. for between about 2 and about 48 hours. It was found that the nucleation of cephalothin sodium crystals was essentially complete between about 12 and about 24 hours from an aqueous concentration of between about 15 and about 33 percent when the frozen mass was held between <0° C. and −10° C. Cephaloridine betaine crystals were essentially, completely nucleated from an aqueous concentration of between about 20 and about 40 percent when a frozen mass of such a preparation was held between <0° C. and −10° C. for between 12 and 48 hours. Cefazolin sodium nucleates much faster at between <0° C. and −10° C., and was essentially complete from an aqueous concentration between about 15 and about 40 percent in between about 2 and about 8 hours.

After the nucleation of the cephalosporin crystals is substantially complete, a conventional freeze-drying operation is utilized to sublime the ice from the frozen mass leaving a deposit of sterile essentially crystalline cephalosporin.

The cephalosporin preparation wherein the nucleation of the crystals is substantially complete is subjected to an environment where the pressure can be reduced to a practical maximum of no more than 1mm mercury absolute. It is preferable to reduce the pressure much more than to a 1mm absolute. The best results are obtained with an absolute pressure of between about 0.05mm and about 0.2mm. This latter pressure range is ordinarily readily attainable in both laboratory and commercial freeze-drying apparatus, the design, construction and operation of which are all well known to those skilled in the art. After the pressure of the environment described above has been reduced to an operating level, heat is introduced into such an environment. The temperature of the environment is raised to a point where the maximum sublimation rate can be achieved without melting the frozen mass. As a general rule, the temperature and the pressure are inversely related; the more effective the pressure reduction, the higher the temperature which can be employed in the subliming operation. As a common guide it can be said that a maximum environment temperature of 50° C. can be reached with a highly efficient vacuum system where the absolute pressure is maintained at about 0.05mm absolute (50µm). In any event, the temperature should be raised slowly so as to avoid overloading the pressure-reducing system which can produce an undesirable melting of the frozen mass. Preferably, the temperature of the environment in the subliming operation should be maintained between from 20° C. and about 40° C. with the pressure held at or below 0.2mm absolute.

Subliming of the ice from the frozen mass is continued until the moisture content of the cephalosporin crystals is below 6 percent. Cephalothin sodium crystals are not hydrated, and it is essential to continue the sublimation until the moisture content is below 1 percent. Such a specification assures physical stability of the resulting crystals. Cephaloridine betaine crystallizes with about one mole of water; and, consequently, the final moisture content of the crystals should be held below about 3.5 percent, which includes the water of hydration. Cefazolin sodium crystallizes as the pentahydrate. Holding the crystals at 25° C–30° C., after the ice has been completely sublimed, converts the penta- to the hemi-hydrate. Such crystals can contain up to about 6 percent moisture.

The cephalosporins prepared as detailed above are essentially crystalline. For example, physical analyses of cephalothin sodium indicated a crystallinity of between about 92 and about 98 percent, cephaloridine betaine was practically 100 percent, and cefazolin sodium hemi-hydrated was greater than 90 percent. In any event, a sufficiently high amount of crystallinity was obtained to impart storage stability; i.e., an absence of a yellowing of the substance, and loss of microbiological potency for up to 3 years at room temperature. These cephalosporin crystals can be sterile filled into previously sterilized ampoules in appropriate quantities for reconstitution for parenteral administration. The three cephalosporins which are involved in the instant invention are all in use today for combatting susceptible pathological organisms in sick people.

In another aspect of this invention the procedure outlined and discussed in detail hereinbefore is augmented by an additional step which comprises filling a measured volume of the sterile aqueous solution from step (b) into a previously sterilized ampoule, such measured volume containing the quantity of the cephalosporin which is desired in such ampoule after the freeze-drying operation. The ampoules containing the sterile aqueous solution of the cephalosporin are then processed in the same manner as described above. The resulting freeze-dried cephalosporin ampoule is ready for sterile stoppering and capping.

In practice it is preferred to sterile fill a measured volume of the sterile aqueous solution into a previously sterilized ampoule as at least two beneficial results are obtained. First, a more precise and consistent quantity of the cephalosporin can be filled into an ampoule in the liquid form than in the solid (crystals or powder) form. And, second, it is much easier to achieve and maintain sterile operating conditions in liquid filling operations than in dry filling operations. Moreover, air pollution is less of a problem when handling liquids than dry materials.

What is claimed is:

1. A method of preparing a sterile, essentially crystalline cephalosporin selected from the group consisting of cephalothin sodium, cephaloridine betaine and cefazolin sodium for reconstitution for parenteral administration comprising the steps of:
   a. dissolving said cephalosporin in water;
   b. filtering the solution from (a) through a sterilizing filter;
   c. cooling the sterile filtrate from (b) rapidly to a temperature below at least −15° C. within an interval not longer than 3 hours;
   d. warming the preparation from (c) to between <0° C. and about −10° C.;

e. maintaining the temperature of the preparation from (d) between <0° C. and about −10° C. until the nucleation of the crystals of said cephalosporin is substantially complete;
f. reducing the pressure of the environment in which the preparation from (e) is maintained to a maximum of 1mm absolute;
g. raising the temperature of the environment in which the preparation from (f) is maintained to a maximum of about 50° C., avoiding the melting of such preparation; and
h. subliming the water from the preparation from (g) until the resulting crystals of said cephalosporin have a moisture content of no more than 6.0 percent.

2. The method according to claim 1 wherein the concentration of the cephalosporin in the aqueous solution is between about 15 and about 40 percent (W/V).

3. The method according to claim 2 wherein the concentration of cephalothin sodium in the aqueous solution is between about 15 and about 33 percent (W/V).

4. The method according to claim 2 wherein the concentration of cephaloridine betaine is between about 20 and about 40 percent (W/V).

5. The method according to claim 2 wherein the concentration of cefazolin sodium in the aqueous solution is between about 15 and about 40 percent (W/V).

6. The method according to claim 1 wherein the preparation from step (d) is maintained between <0° C. and about −10° C. for between about 2 to about 48 hours.

7. The method according to claim 6 wherein when the preparation is cephalothin sodium such preparation is maintained between <0° C. and about −10° C. for between about 12 and about 24 hours.

8. The method according to claim 6 wherein the preparation is cephaloridine betaine such preparation is maintained between <0° C. and about 3110° C. for between about 12 1 and about 48 hours.

9. The method according to claim 6 wherein when the preparation is cefazolin sodium such preparation is maintained between <0° C. and about −10° C. for between about 2 and about 8 hours.

10. The method according to claim 1 wherein the pressure is reduced to between about 0.05 and about 0.20mm of mercury absolute (50 to 200$\mu$m absolute) and the temperature of the environment is raised slowly to between about 0° C. and about 40° C. maintaining an absolute pressure of no more than 0.20 mm or mercury avoiding the melting of said cephalosporin preparation.

11. The method according to claim 1 wherein the sublimation of the water from said cephalosporin preparation is continued until the moisture content of the resulting crystals of said cephalosporin have a moisture content of between about 0.1 and about 6.0 percent.

* * * * *

UNITED STATES PATENT AND TRADEMARK OFFICE
CERTIFICATE OF CORRECTION

PATENT NO. : 4,029,655
DATED : June 14, 1977
INVENTOR(S) : Michael D. Cise

It is certified that error appears in the above-identified patent and that said Letters Patent are hereby corrected as shown below:

Column 8, line 11, "3110°" should be -- -10°--.

Column 8, line 12, "12 1 and" should read --12 and --.

Column 8, line 22, "or mercury" should read --of mercury--.

Signed and Sealed this

Nineteenth Day of June 1979

[SEAL]

Attest:

RUTH C. MASON
Attesting Officer

DONALD W. BANNER
Commissioner of Patents and Trademarks